United States Patent [19]
Chu et al.

[11] Patent Number: 5,989,399
[45] Date of Patent: Nov. 23, 1999

[54] EFFECTIVE SURFACE TREATMENT FOR A NEW SEPARATION MEDIUM IN ELECTROPHORESIS

[75] Inventors: Benjamin Chu, Setauket; Chunhung Wu, Lake Grove, both of N.Y.

[73] Assignee: The Research Foundation of State University of New York, Albany, N.Y.

[21] Appl. No.: 08/892,806

[22] Filed: Jul. 15, 1997

Related U.S. Application Data

[63] Continuation-in-part of application No. 08/707,794, Sep. 4, 1996.

[51] Int. Cl.$^6$ ........................ G01N 27/26; G01N 27/447
[52] U.S. Cl. ........................................ 204/456; 204/605
[58] Field of Search ........................ 204/605, 455, 204/454, 451, 452, 453, 601, 602, 603, 604

[56] References Cited

U.S. PATENT DOCUMENTS

| | | | |
|---|---|---|---|
| 4,582,868 | 4/1986 | Ogawa et al. | 204/469 |
| 4,680,201 | 7/1987 | Hjerten | 204/601 |
| 4,769,408 | 9/1988 | Ogawa et al. | 204/469 |
| 4,812,269 | 3/1989 | Harttig et al. | 264/41 |
| 4,908,112 | 3/1990 | Pace | 204/601 X |
| 4,990,550 | 2/1991 | Iwanami et al. | 523/384 |
| 5,126,021 | 6/1992 | Grossman | 204/601 |
| 5,143,646 | 9/1992 | Nochumson et al. | 204/469 |
| 5,151,464 | 9/1992 | Yang | 524/449 |
| 5,164,055 | 11/1992 | Dubrow | 204/455 |
| 5,167,783 | 12/1992 | Halloway | 204/605 |
| 5,167,784 | 12/1992 | Noolandi | 204/458 |
| 5,213,669 | 5/1993 | Guttman | 204/452 |
| 5,264,101 | 11/1993 | Demorest et al. | 204/452 |
| 5,282,941 | 2/1994 | Rose Jr. | 204/605 |
| 5,290,418 | 3/1994 | Menchen et al. | 204/455 |
| 5,360,855 | 11/1994 | Gobran | 524/274 |
| 5,447,617 | 9/1995 | Shieh | 204/451 |
| 5,468,365 | 11/1995 | Menchen et al. | 204/455 |

FOREIGN PATENT DOCUMENTS 6-273382  9/1994  Japan .

OTHER PUBLICATIONS

Martin Malmsten et al, "Adsorption of PEO–PPO–PEO Block Copoly–mers at Silica" Macromolecules, vol. 35, No. 9, pp. 2474–2481, 1992 *no month available.

Chu, B., *Langmuir* no month available 1995, 11, 414–421.

Tiberg, F., *Langmuir* no month available 1991, 7, 2723–2730.

Malmsten, M., *Macromolecules* no month available 1992, 9, 2474–2481.

*Primary Examiner*—William H. Beisner
*Assistant Examiner*—John S. Starsiak, Jr.
*Attorney, Agent, or Firm*—Hoffman & Baron, LLP

[57] ABSTRACT

A device is described for electrophoretic molecular separation. This device has a channel formed on a hydrophobic surface thereof. The interior surface of the channel is rendered hydrophilic through successive oxidation and protophilic reactions. A cover extends over the channel to form a conduit which is dimensioned to accept a molecular separation media. The conduit is also positioned for application of an electric current along the length of the interior of the conduit which drives a sample through the molecular separation media. Systems and methods are also described for electrophoretic molecular separation.

31 Claims, 4 Drawing Sheets

EFFECTIVE SURFACE TREATMENT FOR A NEW SEPARATION MEDIUM IN ELECTROPHORESIS

CROSS-REFERENCE TO RELATED APPLICATION

This application is a continuation-in-part of U.S. Ser. No. 08/707,794, filed Sep. 4, 1996, which is incorporated by reference herein.

The present invention has resulted from investigatory work supported by U.S. Government funds provided under NIH: National Center for Genome Research (1R01HG0138601); NSF: MRSEC for Engineered Polymer Interfaces (DMR9632525; and Biotechnology Center of the State of New York (X310N). The government has certain rights in the invention.

BACKGROUND OF THE INVENTION

The present invention relates generally to the art of separating charged molecular species, and, in particular, to new devices, systems and methods for practicing same.

Capillary gel electrophoresis is one of the most widely used separation techniques in the biologically related sciences. Charged molecular species such as proteins, peptides, nucleic acids, amino acids and oligonucleotides are separated by causing the species to migrate in a buffer medium under the influence of an electric field. The buffer medium normally is used in conjunction with a low to moderate concentration of an appropriate gelling agent, such as for example, agarose or cross-linked polyacrylamide, to promote the separation and to minimize the occurrence of mixing of the species being separated.

Until recently, electrophoretic separations were conducted in gel slabs or open gel beds which were typically fabricated of agarose or cross-linked polyacrylamide material. More recently, capillary gel electrophoresis techniques combined with photometric detection methods have allowed the automation and rapid quantitative analysis of charged molecules. Furthermore, capillary gel electrophoresis can provide quantitative information about a sample using very small amounts of the sample, gel and buffer relative to traditional slab gel processes. Moreover, high resolution separation of molecules having different effective charges have been achieved by applying electrophoretic principles to polymer solution-filled or gel-filled narrow capillary tubes.

A problem encountered with such separation methods is the compatibility of a particular separation medium with the surface of the separation device. In particular, electro-osmotic flow of a sample to be separated between the separation medium and the inner surface of the separation device occurs when a separation medium is unable to adhere, i.e., adsorb, to the surface of the separation device. Such electro-osmotic flow provides unreliable separation results because the sample flows around the separation medium instead of through it.

Traditional methods aimed at preventing such electro-osmosis include introducing a compound which binds to the inner surface of a capillary tube wall, as well as, to the separation medium prior to injecting the separation medium into the tube. For example, U.S. Pat. No. 5,447,617 to Shieh describes covalently bonding polybutadiene to the inner surface of a capillary tube, introducing polyacrylamide therein and co-polymerizing the polyacrylamide with the polybutadiene. Such precoating techniques, however, are time consuming, inconvenient and costly.

A further problem of conventional capillary gel electrophoresis is encountered with the use of polyacrylamide-based separation media. Such media are injected into the capillary tube in unpolymerized form. Polymerization of the polyacrylamide is then induced within the capillary tube by any number of methods including ultraviolet radiation and chemical catalysts. Such methods are characterized by a lack of uniformity in the pore size distribution of the polymer network formed, and by incomplete polymerization.

Accordingly, attempts have been made to use nonpolymerized separation media for capillary gel electrophoresis. See for example, U.S. Pat. Nos. 5,126,021, 5,468,365 and 5,213,669 which describe separation media which form dynamic entanglements, associations, or cross-links for electrophoretically separating biological samples including protein, DNA and RNA. These separation media are not ideal for separating molecular samples because they are difficult to manipulate, require precoating of the surface of the separation device and/or are not universally compatible with the surface of such separation devices, i.e., do not have temperature-dependant hydrophobic and hydrophilic segments, respectively.

Glass and silica surfaces are most commonly used in conjunction with the separation media described above. For example, capillary columns used in capillary gel electrophoresis are fabricated from lengths of fused silica tubing having diameters on the order of 25 $\mu$m to 200 $\mu$m and lengths from about 30 cm to about 200 cm. The buffer and gel separation media are pumped directly into the column interiors and electrophoretic techniques are used to separate charged molecular species.

Similarly, such molecular separations have been attempted on the surface of silicon wafers. For example, U.S. Pat. No. 4,908,112 to Pace, hereby incorporated by reference, discloses an analytical separation device in which a capillary sized, i.e., micro-machined conduit is formed by a channel in a semiconductor device. The surface of such a device is conditioned to accept traditional separation media. In particular, the surface of the semiconductor device is thermally oxidized to form a $SiO_2$ layer. The conduit is then filled with a traditional electrophoretic gel preparation fluid, such as for example, a monomer and a cross-linker of a polyacrylamide.

A major drawback to the use of such a device, however, is the inability of many separation media to adhere/adsorb to the inner wall of the conduit which, as set forth above, creates electro-osmotic flow of a sample between the surface of the gel and the wall of the conduit when an electric field is applied during electrophoresis. When such electro-osmotic flow of the sample occurs, a satisfactory separation of the constituent parts of the sample cannot be obtained.

Thus, attempts have been made to find separation media capable of high adsorbency onto, e.g., silica surfaces, and which are still able to electrophoretically separate molecular species. In particular, the adsorption of nonionic block copolymers of the Pluronic PE type, i.e., poly(oxyethylene)-poly(oxypropylene)-poly(oxyethylene), at hydrophobic silica surfaces have been investigated. See for example, Teberg, F.; Malmsten, M.; Linse, P.; Lindman, B. *Langmuir,* 1991, 7, 2723–2730 and Malmsten, M.; Linse, P.; Cosgrove, T. *Macromolecules,* 1992, 25, 2474–2481. The utility of such media, however, is limited by the requirement that the silica surfaces of the separation device be rendered hydrophilic for effective adsorbency thereon by the oxyethylene (E) block of the separation media.

Accordingly, it would be desirable to provide a device for electrophoretic molecular separation that is adapted to accept a molecular separation medium which efficiently and effectively separates molecular species without the problems associated with the above-referenced citations. It would also be desirable to provide a separation medium with the ability to adsorb to a variety of substrate surfaces and to change between liquid and gel-like states for efficient application and removal of the medium from such a molecular separation device. In particular, it would be desirable to provide a device for molecular separation which has a surface with hydrophobic properties which surface can be modified to accept such a molecular separation medium through successive oxidation and protophilic reactions. It would also be desirable to provide methods for rendering hydrophilic surfaces, such as silicon surfaces, competent to receive molecular separation media.

SUMMARY OF THE INVENTION

The present invention includes a device for electrophoretic molecular separation. This device has a channel formed on a hydrophobic surface thereof. The interior surface of the channel is rendered hydrophilic through successive oxidation and protophilic reactions. A cover extends over the channel to form a conduit which is dimensioned to accept a molecular separation media. The conduit is also positioned for application of an electric current along the length of the interior of the conduit which drives a sample through the molecular separation media.

Other embodiments of the present invention include a method of making a molecular separation device and a system for molecular separation. Both embodiments utilize a channel formed on the surface of a hydrophilic substrate which is subsequently treated with an oxidizing agent and a protophilic agent in order to receive and retain a molecular separation medium therein. A cover spans and/or is fixed over the channel to form a conduit in which the molecular separation occurs when an electrophoretic charge is allowed to pass therethrough.

A further embodiment of the present invention is a method of rendering a device having a hydrophobic surface competent to separate molecular species. This method includes sequentially treating the hydrophobic surface with an oxidizing agent and a protophilic agent, respectively.

Another embodiment of the present invention is a channel for electrophoretic molecular separation. This channel has a hydrophobic surface which is rendered hydrophilic through successive oxidation and protophilic reactions. This channel can be formed on a surface of a silicon wafer or a layer of silicon may be disposed on the channel surface to render it hydrophobic.

Still further, another embodiment of the present invention is a method for rendering a device having a hydrophobic surface competent to separate molecular species. This method includes treating the hydrophobic surface with an oxidizing agent and then with a protophilic agent to render the surface hydrophilic.

Preferably, the device of the present invention is a silicon wafer. As set forth above, the surface of such a device is treated with an oxidizing agent which includes hydrogen fluoride, ozone, permanganate ion, nitric acid, oxygen and mixtures thereof. The oxidizing agent provides the conduit formed on the surface of the separation device with a silica ($SiO_2$) surface. An acid is then used to produce the protophilic reaction which renders the silica surface hydrophilic (SiOH). Preferably, the oxidation and protophilic reactions are produced with HF and HCl, respectively.

The present invention also includes a mechanism for providing an electrophoretic charge between the first and second ends of the conduit which are spaced apart. Such a mechanism preferably includes an anode and a cathode at the first and second ends of the conduit, respectively.

The molecular separation medium of the present invention includes at least one block copolymer which is in solution at a first operating temperature and is in a gel-like state at a second operating temperature. This medium includes an operating buffer which dissolves the block copolymer at the first operating temperature and remains in the medium in the gel-like state without disruption of the molecular separation. The operating buffer renders the block copolymer dissolute upon return to the first operating temperature.

In the various embodiments of the present invention, the molecular separation medium is introduced within the conduit. This medium, when it is in its gel-like state, is adherent to, i.e., adsorbs to, the surface of the conduit and prevents electro-osmotic flow of a sample at an interphase between the medium and the conduit surfaces.

Although at least one block copolymer of the molecular separation medium is required to practice the present invention, at least one additional block copolymer may be added thereto. Furthermore, the block copolymers of the present invention may be selected from di-block copolymers, tri-block copolymers, multi-block copolymers and mixtures thereof. Moreover, these block copolymers are further defined by the following formulae: (I) $A_xB_y$; (II) $A_xB_yA_z$; (III) $B_xA_yB_z$; (IV) $A_xB_yC_z$; and mixtures thereof wherein A, B and C are independently selected from the group consisting of poly(oxyethylene), poly(oxypropylene), poly(oxybutylene), polyacrylamide and poly(isopropyl) acrylamide; and x, y, and z are independently selected from whole numbers from about 1–10,000.

Preferably, at least one of the block copolymers is $E_{41}B_8$, $E_{99}P_{69}E_{99}$, $B_{12}E_{260}B_{12}$, $E_{45}B_{14}E_{45}$, $E_{132}P_{56}E_{132}$, $E_{79}B_{36}E_{79}$, and mixtures thereof wherein E is poly(oxyethylene), P is poly(oxypropylene) and B is poly(oxybutylene).

As stated hereinabove, the molecular separation medium includes an operating buffer. Preferably, the operating buffer is, for example, a good solvent for a first block segment of the block copolymer and is a marginal, a poor or a nonsolvent for a second block of the block copolymer. In such a buffer, the marginally solvated, poorly solvated, or nonsolvated block segments of the block copolymer self-assemble. Preferred operating buffers include 1× TBE and tris-glycine buffers. A preferred viscosity-adjustable medium of the present invention includes, for example, about 25% (w/v) of $E_{99}P_{69}E_{99}$ in 1× TBE buffer.

Preferably, the first operating temperature is outside of the operative temperature for electrophoresis; whereas, the second operating temperature is about at the operative temperature for electrophoresis. More preferably, for the EP- or EB-type copolymers, the first operating temperature is from about 15° C. to about 1° C.; whereas, the second operating temperature is above about 20° C. For other types of copolymers, the first and second operating temperatures will vary. Such temperatures are determined with reference to the specific copolymers selected, as well as, the particular application. Such determinations are within the knowledge of one skilled in the art.

As a result of the present invention, the molecular separation device provides reproducible and reliable molecular separations when used in conjunction with the separation media disclosed herein by preventing electro-osmotic flow of a sample between the walls of the conduit and the surface of the separation media. Furthermore, the viscosity-adjustable nature of the present molecular separation media allows for the quick and efficient isolation and retrieval of electrophoretically separated components. Moreover, the methods and systems of the invention are economical and can be readily integrated into existing systems. Still further, the molecular separation media are quickly and efficiently introduced to, and removed from, for example, molecular separation devices contained on the surface of silicon wafers.

These and other advantages will become apparent to the skilled artisan in view of the disclosure set forth herein.

DETAILED DESCRIPTION OF THE PREFERRED EMBODIMENTS

Figure 1:
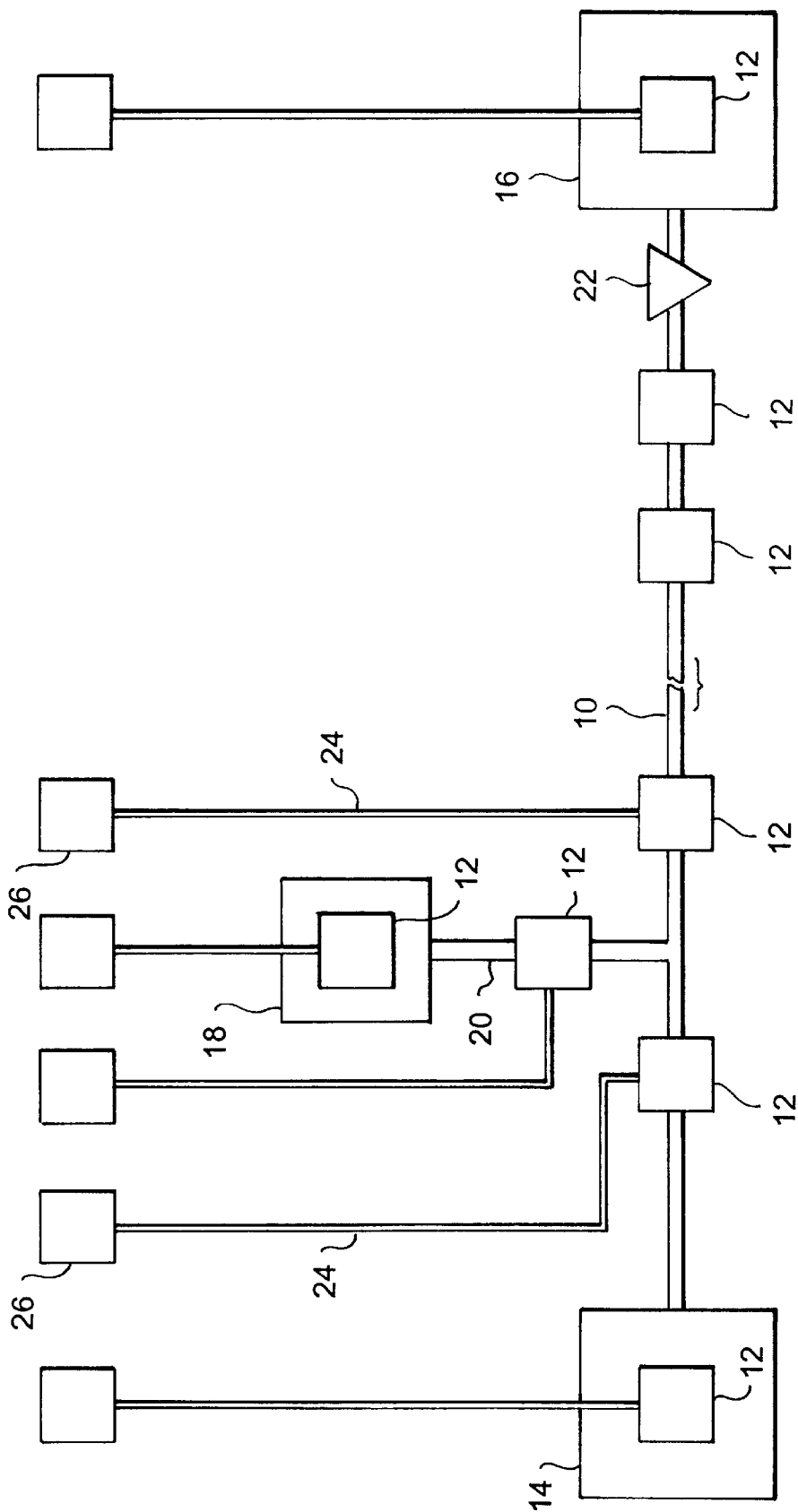
FIG. 1 shows a schematic representation of a molecular separation device constructed in accordance with the present invention.

The present invention includes a device for molecular separation utilizing, for example, electrophoretic and chromatographic techniques. This device contains a substrate having hydrophobic properties. A channel having an interior surface is formed on the surface of the substrate. For purposes of the present invention, "channel" refers to capillary sized conduits constructed from semi-conductor or polymeric materials using conduit dimensions appropriate for molecular separations. The fabrication methods used in generating such conduits are those methods generally applied by the semi-conductor or plastic industry. Moreover, the diameter of such conduits is on the order of about 25 $\mu$m to about 200 $\mu$m. Furthermore, conduit dimensions and geometries favorable for electrophoretic and chromatographic separations may be structured on semiconductor and electrical insulator materials known in the art. Such materials include polymer, glass, silicon, germanium and metal oxides.

Preferably, single crystal structural materials, such as silicon, are used to form the present molecular separation device because very precise features may be micromachined onto the surfaces thereof. Moreover, the use of a silicon crystal is preferred because (1) it is obtainable in useful dimensions, such as for example 100 mm diameter and 500 $\mu$m thickness; (2) it has high thermal conductivity; (3) it is harder than steel; (4) it may be modified to an insulator or a conductor; (5) it develops electro-osmotic pressure with aqueous electrolytes; and (6) electronic and electro-optic components may be fabricated on its surface.

The surface of a silicon wafer is naturally hydrophobic. Such a hydrophobic surface must be modified to accommodate separation media which are able to adhere to, i.e., adsorb to the modified silicon surface to prevent electro-osmotic flow of a sample around the separation media instead of through it. Thus, the interior surface of a channel formed on, for example, a silicon crystal, is rendered hydrophilic through successive oxidation and protophilic reactions. For purposes of the present invention, "oxidation reaction" refers to the addition of oxygen to a hydrophobic surface of the molecular separation device. More generally, as used herein, oxidation refers to the loss of electrons from an atom which is always accompanied by a reduction. In the present invention, for example, a silicon (Si) surface is oxidized to a silica ($SiO_2$) surface by use of an oxidizing agent. A consequence of the use of such agents is the etching and cleaning of the silicon surface. Exemplary oxidizing agents useful in the present invention include, for example, hydrogen fluoride, ozone, permanganate ion, nitric acid, oxygen and mixtures thereof.

For purposes of the present invention, "protophilic" or "protophilic reaction" refers to the use of a composition to provide an ionizable hydrogen to the oxidized surface of the molecular separation device. The protophilic reactions of the present invention are accomplished using hydrogen-donating compositions, such as for example, acids. In the present invention, for example, the silica ($SiO_2$) surface is acid-treated to form a hydrophilic silanol (SiOH) surface. Exemplary strong acids which can be used in the protophilic reactions include, with out limitation, hydrochloric acid, nitric acid, sulfuric acid and the like. Preferably, these reactions are carried out with hydrogen fluoride and hydrochloric acid, respectively.

These oxidation and protophilic reactions may be targeted to the channel surface alone or to the entire device. Such reactions are accomplished using standard techniques in the art, such as for example, dipping, spraying, vapor deposition techniques, and the like. Furthermore, the oxidation reaction of the present invention may be carried out, for example, using a modified Shiraki treatment. The protophilic reaction may be carried out, for example, in 1N HCl as set forth in more detail in Example 2 hereinbelow.

Although the molecular separation media of the present invention are able to form micelles on silicon surfaces subjected to the modified Shiraki treatment only (i.e., $SiO_2$ surfaces), larger micelles are formed on silicon surfaces which are subject to both Shiraki and HCl treatments (i.e., SiOH surfaces). In particular, a 1% EPE separation media of the present invention formed larger, more uniform micellar layers on the Shiraki-HCl treated silicon surface as compared to a surface modified by the Shiraki treatment alone.

Furthermore, there appears to be a concentration effect exhibited by the present molecular separation media for the Shiraki-HCl treated silicon surfaces (SiOH). In particular, a 21.2% $E_{99}P_{69}E_{99}$ polymer in water solution forms larger, more-uniform micelles on such surfaces than a 10.6% solution of the same polymer on the same surface. Although the present invention is described in terms of the preferred hydrophobic starting material silicon, processes for rending hydrophobic surfaces hydrophilic disclosed herein are not limited only to silicon surfaces. Accordingly, any hydrophobic surface which can be made hydrophilic through reactions with the oxidation and protophilic reagents set forth herein may be used in the present invention.

Figure 2:
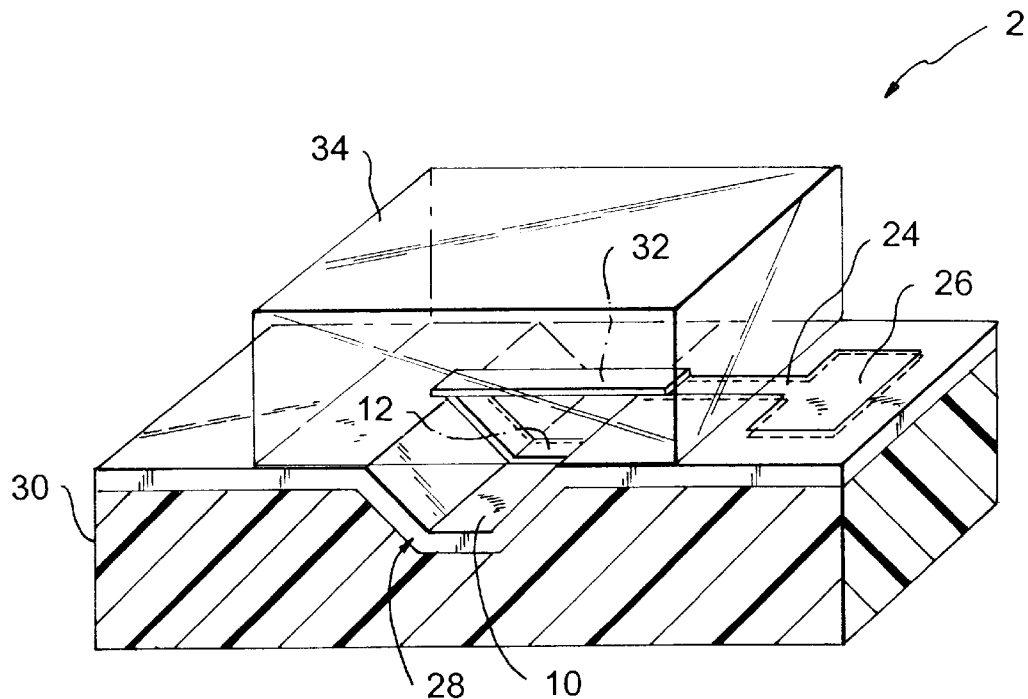
FIG. 2 shows a cross-sectional view of a conduit formed from a channel and a cover in accordance with the present invention.
Figure 3:
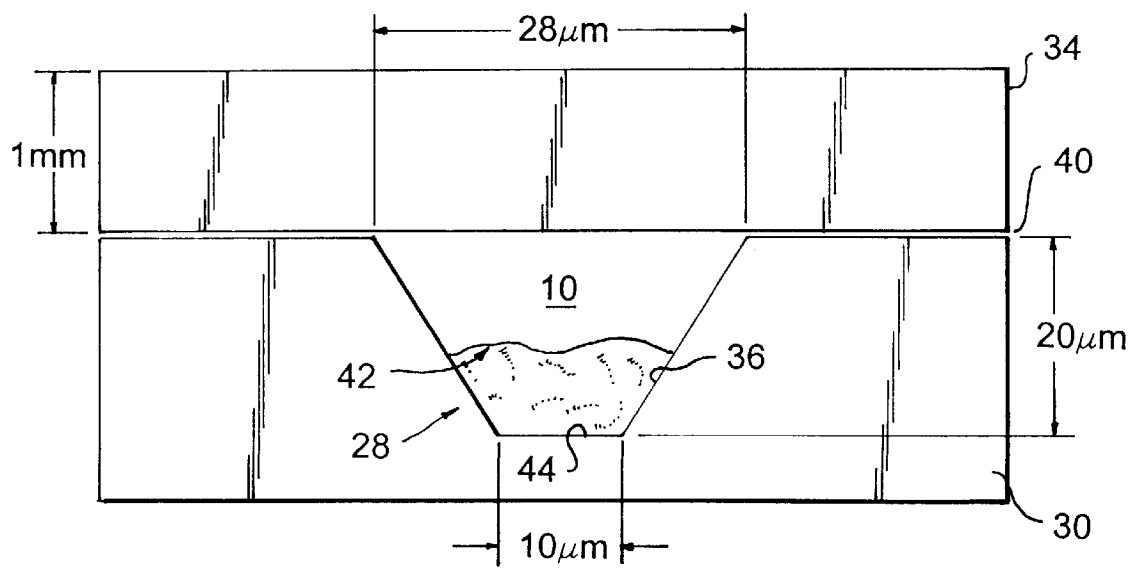
FIG. 3 shows the dimensions of the conduit shown in FIG. 2.
Figure 4:
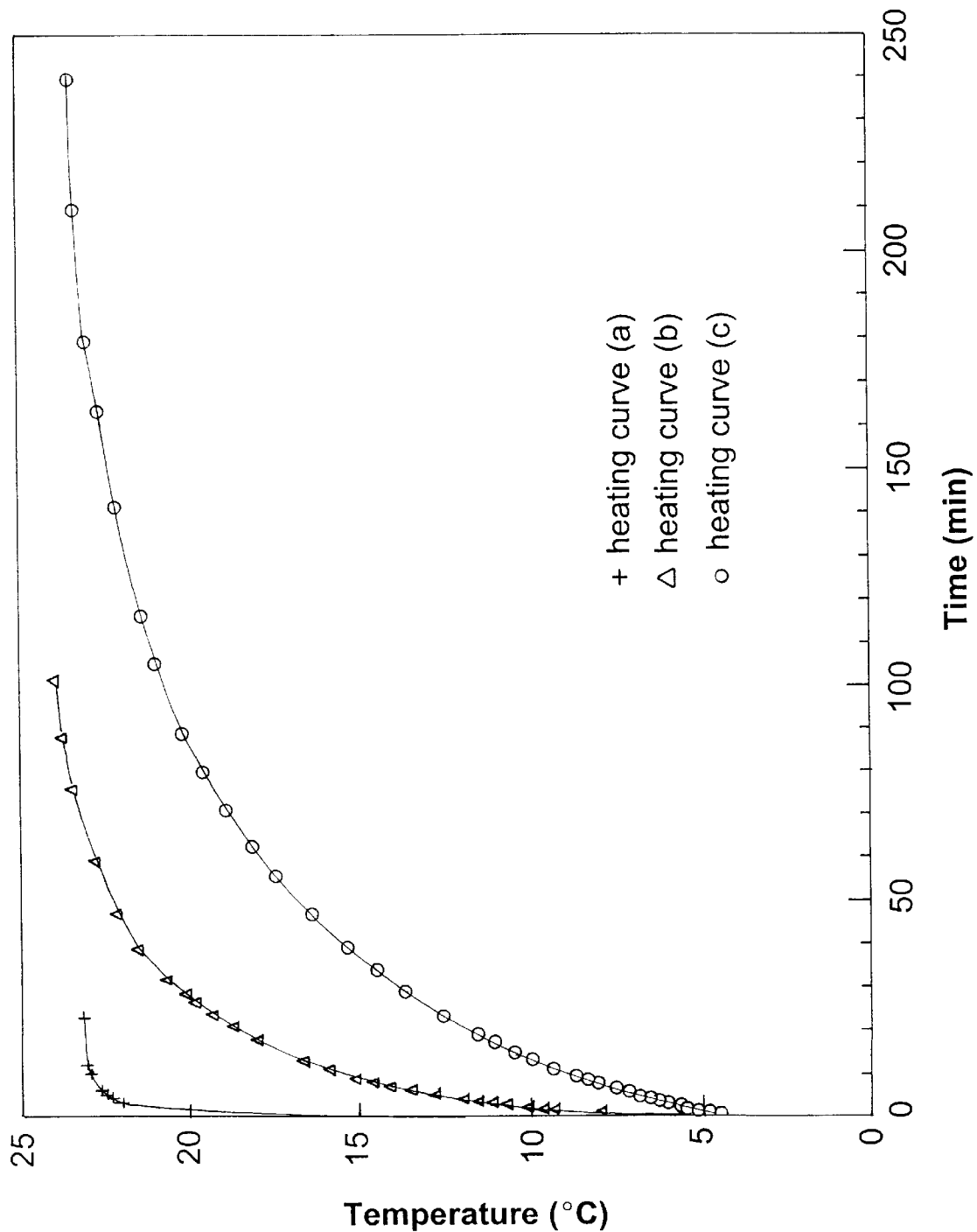
FIG. 4 shows heating curves of three preparations of the viscosity-adjustable molecular separation media of the present invention.

Now turning to FIGS. 2 and 3, the device 2 of the present invention includes a cover 34 which extends over, and is secured to a channel 28 to complete the formation of a conduit 10. The cover 34 is made from any material that is compatible with molecular separation by electrophoretic or chromatographic techniques. Preferably, the cover 34 is made from a transparent material, such as for example fused silica (hereinafter referred to as "glass"), that will allow visual inspection of the conduit 10 and/or spectrophotometric detection therethrough. The cover 34 can be of any dimension suitable for molecular separation in the present invention. Typically, however, a 1 mm thick cover 34 is used with a circular silicon wafer 30 which is 100 mm in diameter and 500 μm thick. The glass cover 34 is bonded to the silicon surface of the molecular separation device 2 and sealed at the top edge of the channel 28 to prevent liquid leaks.

A gasket 40 may be used to bond the silicon wafer 30 to the glass cover 34 and to prevent leakage beyond the confines of the conduit 10 formed by the cover 34 and the channel 28. The gasket 40 may be fabricated from any material provided that it is able to prevent leakage from between the channel 28 and the glass cover 34 and does not interfere with the molecular separation. Preferably, 8 μm thick polyimide gaskets 40 are used which can withstand a sixty percent compression particularly in the region of the electrodes 12. The polyimide gasket 40 is positioned along the top edges of the channel 28 to effect a liquid tight seal.

The conduit 10 formed by the cover 34 and the channel 28 is dimensioned to accept a molecular separation medium 42, as described in more detail below, which is disposed therethrough and which is positioned for application of an electric potential along the length of the interior of the conduit 10. For purposes of the present invention, the conduit 10 is constructed, for example, by forming a channel or channels 28 in a silicon wafer or slab 30.

As set forth above, a typical silicon wafer 30 used in the present invention is 500 μm thick and 100 mm in diameter. Such a wafer will yield channels 28 that may be as much as 80 mm long. These channels may be configured in many different ways to increase the length thereof. For example, the channels may follow tortuous, serpentine-like paths if longer channels are desired. Thus, a typical silicon wafer which is 100 mm in diameter can provide several channels of varying lengths, each adapted to carry out molecular separations as described above. The channel 28 is micromachined to have, for example, a trapezoidal cross-section.

With reference to FIG. 3, a typical channel 28 may be 10 μm wide at the bottom, 28 μm wide at the top, and 20 μm deep. Access holes (not shown) may be formed in the glass cover 34 over each reservoir 14, 16 to permit introduction of a buffer and/or a sample into the device.

Although the above-described trapezoidal channel geometry is preferred, alternate channel geometries may be used in the present invention, such as for example, rectangular, semi-circular and V-shaped geometries. Trapezoidal geometries are preferred because they are most accommodating to light and fluorescence detection schemes as described in U.S. Pat. No. 4,908,112 to Pace. Furthermore, with respect to the above-referenced geometries, sharp corners should be avoided.

With reference to FIG. 1, electrodes 12 are implanted within the channel 28 and are connected to bond pads 26 by respective conductor leads 12. Electrical connections to external instruments and power supplies may be attached to the bond pads 26. The electrodes 12 are positioned at intervals along the length of the conduit 10 and in each reservoir 14, 16 respectively. By positioning the electrodes 12 in this manner, the efficiency and speed of the molecular separation is increased relative to placement of a single electrode at each end of the conduit. At the same time, the amount of voltage required to carry out such separations is decreased which reduces the amount of heat generated.

An auxiliary electrode 32 is formed on the underside of the glass cover 34 prior to securing it to the silicon wafer 30 so that the electrode 32 has maximal contact with the molecular separation medium 42 therein. The auxiliary electrode 32 formed on the glass cover 34 may extend slightly beyond the dimension of the channel 28 to afford good contact with the conductor lead 24.

The bond pads 26, conductor leads 24 and electrodes 12 are all formed by conventional methods, such as for example, by vapor depositing a conductive material directly onto the surface of the silicon wafer 30 or the glass cover 34, respectively. Gold is the preferred conductive material for this purpose, although other conductive materials known in the semi-conductor industry may be used. Such conductive materials include for example, tungsten, silver, copper, platinum, and the like. Although the present invention is described in terms of a preferred molecular separation device, other conventional device configurations may be used as long as the surface of the device on which the molecular separation media is disposed can be modified in accordance with the processes set forth herein to prevent electro-osmotic flow of sample.

Furthermore, any process known in the art may be used to form the device of the present invention as long as the process is compatible with the present oxidation and protophilic reactions and results in a surface to which the present molecular separation media are able to adhere. One process for forming the channel 28 of the present device 2 onto the surface of a silicon wafer 30 includes (1) developing a desired channel and reservoir pattern by photolithography on a photo mask; (2) developing an etch protect mask pattern on an oriented single crystal silicon wafer 30; (3) implanting boron at approximately $10^{20}$ atoms/cm$^3$ at a prescribed depth in the wafer 30 as an etch stop; (4) anisotropically etching exposed silicon with ethylene diamine pyrocatechol in water or using a timed etch instead of the etch stop; (5) oxidizing the surface of the silicon wafer 30 to silica; (6) treating the oxidized silica surface with an acid to render the surface hydrophilic; (7) establishing a desired mask pattern for the lead conductors 24, electrodes 12 and bond pads 26 using suitable photo-tools; (8) vapor depositing a conductive material, such as for example gold, on the unmasked portions of the wafer 30 to form the lead conductors 24, electrodes 12 and bond pads 26; (9) etching or ultrasonically drilling access holes in the glass cover 34; (10) placing, for example, a polyimide "gasket" pattern 40 onto the silicon surface; and (11) pressure bonding the glass cover 34 to the silicon wafer 30.

To use the molecular separation device 2 of the present invention, a molecular separation medium 42 as described in more detail below is introduced into the channel 28 as a solution. For example, this separation medium 42 may be injected into the buffer reservoir 14 and fills the channel 28 up to the recipient reservoir 16. The separation medium 42 is then caused to change to its gel-like state. The buffer and recipient reservoirs 14 and 16, respectively are then filled with an appropriate buffer. A sample is then introduced into the sample channel 18 using, for example a 50 μl gas-chromatography-type syringe. The sample is introduced into an injection conduit 20 by applying a voltage between sample channel 18 and one of the down stream electrodes 12. Excess sample is returned to sample reservoir 26 by reverse voltage applied to the sample chamber 18 and down stream electrodes 12. The sample is then separated by electrophoresis by applying a voltage to the electrode at buffer reservoir 14 (cathode) and the electrode 12 at the recipient reservoir (anode).

As described in co-owned U.S. Ser. No. 08/707,794, the present molecular separation media are known to work successfully with separation devices having hydrophilic surfaces, such as, quartz capillary tubings used for DNA capillary electrophoresis. When a molecular separation device, as described above, has a hydrophobic surface, however, it must be modified as previously described herein to a hydrophilic surface in order to achieve proper adhesion between the gel-like molecular separation medium 42 of the present invention and the modified surface of the channel 28. Care must be taken to ensure such adhesion to prevent electro-osmotic flow of a sample between a surface of the gel-like medium 42 and a surface the channel 28 of the separation device 2.

The modification of the channel surface includes a two-step process as set forth previously by which the hydrophobic surface of, e.g., a silicon wafer, is oxidized to silica and then modified to hydrophilic silanol through a subsequent acid treatment. The separation media according to the present invention are able to adhere to surfaces treated in this manner. In particular, in their gel-like states, the supra molecular EP and EB compositions according to the present invention effectively adhere to such modified surfaces as demonstrated by atomic force microscopy (AFM), dynamic light scatter (DLS) and small angle x-ray scatter (SAXS) techniques. Accordingly, the molecular separation device 2 and the molecular separation media 42 of the present invention are highly effective for separating charged molecular species, such as for example, natural occurring or synthetically derived proteins, peptides, nucleic acids, amino acids and nucleotides. The present invention is particularly well suited for separating DNA, RNA, their analogs, derivatives and fragments.

The molecular separation medium used in connection with the molecular separation device set forth above is a viscosity-adjustable medium which relies on at least one block copolymer in an operating buffer. For purposes of the present invention, "viscosity-adjustable medium" refers to a solution containing one or more of the block copolymers described hereinbelow in a selective operating buffer which is a good solvent for one of the segments of the block copolymer but a marginal solvent, a poor solvent or a nonsolvent for another of the segments of the block copolymer at the operative temperature for electrophoresis. By varying the temperature of these block copolymers, the present molecular separation medium is able to change its physical structure between a low viscosity solution and a gel-like matrix.

In particular, at a first operating temperature the block copolymer solution of the present invention has a low solution viscosity which makes it very easy to dispense the solution into, for example, the buffer reservoir 14 and channel 28 of the previously described molecular separation device. In addition, when the molecular separation media of the present invention are in their low solution viscosity state, they are easily manipulatable using, for example, pipettes and syringes.

For purposes of the present invention, "gel-like state" means a state which has the appearance and consistency of a gel but is further characterized by the ability of the block copolymers within the separation medium to dynamically self-assemble and disassemble wherein substantially all of the block copolymers are self-assembled at any one time. In the self-assembled state, the block copolymers form gel-like networks with predetermined microstructures which are able to be adsorbed to the surface of the channel 28 of the molecular separation device 2 and are able to prevent electro-osmotic flow of a sample between a surface of the channel 28 and a surface of the gel-like separation media 42. Accordingly, such separation media are able to accurately and effectively separate charged molecules.

As used in the present invention, "first operating temperature" refers to a temperature which is not destructive of the present block copolymer medium and which is characterized by a low solution viscosity of the block copolymer medium. At such a low solution viscosity, the block copolymer medium can be easily introduced into, for example, the molecular separation device 2, without destruction of the block copolymers.

"Second operating temperature" as used in the present invention means a temperature at which the block copolymer medium exists in a gel-like state which is able to provide the desired separation of charged molecules. This second operating temperature does not destroy the block copolymer medium or the sample; nor does it prevent the block copolymer medium from returning to the low solution viscosity state. Thus, by changing the temperature of the block copolymer medium of the present invention between the first operating temperature and the second operating temperature, the viscosity and structure of the medium can be adjusted between a low viscosity solution and a gel-like matrix.

As set forth hereinabove, the block copolymers of the present invention are characterized by their ability to self-assemble into a gel-like matrix which is suitable for, e.g., separation of charged molecules during electrophoresis. The structure and properties of these block copolymers can vary depending upon the total chain length, the block length ratio, the block sequence, and the buffer. For example, a variety of self-assembled structures can be created with the block copolymers of the invention which range from core/shell micelles, such as for example AB or ABA block copolymers or flower-like micelles, such as for example BAB tri-block copolymers to branched and network-like structures, such as for example, BAB tri-block copolymers having a long middle soluble A block.

For purposes of the present invention, "operating buffer" means a solution that is a good solvent for one of the block segments of the block copolymer but is a marginal solvent, a poor solvent or a nonsolvent for another block segment. Furthermore, the operating buffer of the present invention must not destroy either the block copolymers dissolved therein or the sample to be separated. Moreover, the operating buffer must remain functional at both the first and second operating temperatures. By "functional" it is meant that the buffer retains its ability to dissolve the copolymers at the first operating temperature and does not interfere with the ability of the block copolymers to self-assemble into the gel-like state at the second operating temperature. Furthermore, the buffer must not interfere with the ability of the block copolymers to adhere to the modified surface of the channel 28.

The molecular separation medium may contain at least one additional block copolymer. The block copolymers of the present invention can be any block copolymer that is capable of forming a viscosity-adjustable medium in an operating buffer and which is able to adsorb to a hydrophillic surface, such as, the surface-modified channel 28 of the present invention. Preferred block copolymers include for example, di-block copolymers, tri-block copolymers and mixtures thereof.

The molecular separation medium of the present invention contains at least one block copolymer which may be described by the following formulae:

Formula (I) $A_xB_y$;

Formula (II) $A_xB_yA_z$;

Formula (III) $B_xA_yB_z$;

Formula (IV) $A_xB_yC_z$ and mixtures thereof, wherein A, B and C are independently selected from the group consisting of poly(oxyethylene), poly(oxypropylene), poly(oxybutylene), polyacrylamide and poly(isopropyl) acrylamide; and x, y, and z are independently selected from whole numbers from about 1–10,000.

At least one of the block copolymers of the present molecular separation medium is selected from the group consisting of $E_{41}B_8$, $E_{99}P_{69}E_{99}$, $B_{12}E_{260}B_{12}$, $E_{45}B_{14}E_{45}$, $E_{132}P_{56}E_{132}$, $E_{79}B_{36}E_{79}$, and mixtures thereof wherein E is poly(oxyethylene), P is poly(oxypropylene) and B is poly(oxybutylene).

In the present invention, the operating buffer is a good solvent for a first block segment of a block copolymer and a marginal, poor or nonsolvent for a second block of the block copolymer. The marginally solvated, poorly solvated, or non-solvated block segments of the present invention self-assemble and form supramolecules. Beyond its overlap concentration, these supramolecules form gel-like networks through which charged molecules will migrate when an electric field is applied. In this way, the charged molecules are separated based on size and charge density.

Suitable operating buffers of the present invention include, for example, tris(hydroxymethyl)aminomethane, 2-N-(morpholine) ethanesulfonic acid, N-(2-acetamido) iminodiacetic acid, piperazine-N,N'-bis(2-ethanesulfonic acid, N(2-acetamido)-2-aminoethanesulfonic acid, (2-aminoethyl) trimethyl-ammonium chloride hydrochloride, N,N-bis(2-hydroxy-ethyl)-2-aminoethane sulfonic acid, N-2-hydroxy-ethylpiperazine-N'-2-ethanesulfonic acid, N-tris(hydroxyl-methyl)methylglycine, N,N-bis(2-hydroxyethyl)-glycine, 2-(N-cyclohexylamino) ethanesulfonic acid and mixtures thereof. Preferably, the operating buffer is 1× TBE buffer which is about 89 mM tris(hydroxymethyl)aminomethane, about 89 mM boric acid, about 2 mM ethylenediaminetetraacetic acid (EDTA) in deionized water. In one embodiment of the present invention, the viscosity-adjustable medium includes about 25%(w/v) of $E_{99}P_{69}E_{99}$ in 1× TBE buffer.

As set forth hereinabove, the first operating temperature is a temperature outside of the normal operating temperature range for separation of charged molecules using, for example, electrophoresis. In the present invention, the first operating temperature cab be below the operating temperature of, e.g., electrophoresis. In this embodiment, the first operating temperature is below about 20° C. Preferably, the first operating temperature is from about 15° C. to about 1° C. More preferably, the first operating temperature is about 4° C.

In the present invention, the first operating temperature can also be above the operating temperature of, for example, electrophoresis. When this occurs, a requirement with respect to the temperature range for the first operating temperature is that the molecular separation medium be in a liquid state and have a relatively low viscosity for easier fluid manipulation. Thus, the first operating temperature is determined by the physical properties of the particular block copolymers and operating buffer used. For example, a molecular separation medium composed of 15% (w/v) $E_{79}B_{36}E_{79}$ has a low solution viscosity at a first operating temperature of about 40° C.; whereas it is gel-like at a second operating temperature of about 25° C.

For purposes of the present invention, the second operating temperature corresponds to that temperature at which the molecular separation medium forms a gel-like polymer network. Like the first operating temperature, the second operating temperature is determined by the copolymer composition and the buffer used to make the molecular separation medium of the present invention. Preferably, the second operating temperature is above about 20° C., such as for example, at the operative temperature for electrophoresis.

Figure 5A:
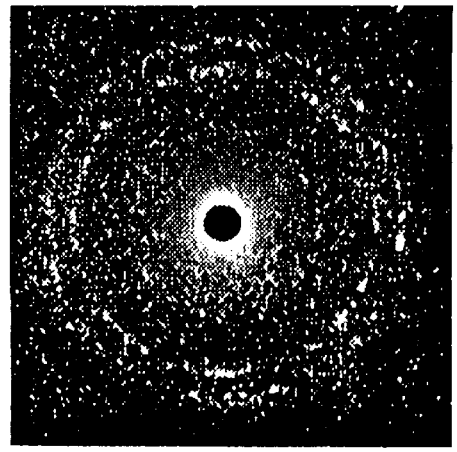
FIG. 5 show a synchrotron small angle x-ray scattering picture of the three preparations of FIG. 4.
Figure 5B:
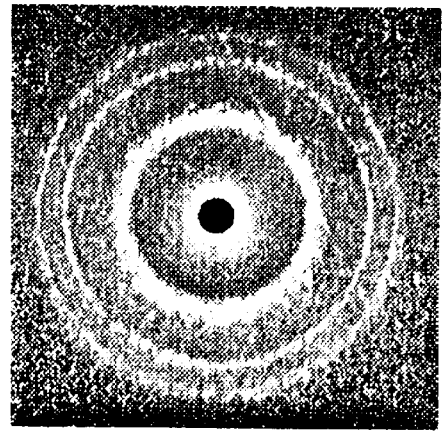
Figure 5C:
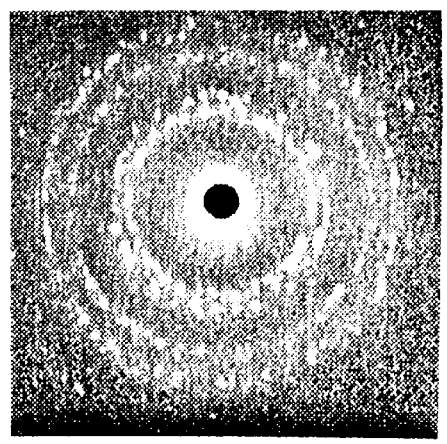

The rate at which the molecular separation medium is brought from the first operating temperature to the second operating temperature effects the molecular order of the gel-like state. In particular, FIG. 5 shows heating curves of three separation media of 25% (w/v) F127 ($E_{99}P_{69}E_{99}$) as the temperature is raised from 4° C. to 25° C. at three different rates (a, b, and c). FIG. 6 shows a synchrotron small angle x-ray scattering (SAXS) picture of the molecular order of the three gels (a, b, c) after being subjected to the three different heating rates shown in FIG. 5. It is clear from FIG. 6 that the molecular structure of the gel-like state is more ordered with the slower heating rate. Furthermore, at higher operating temperatures, the molecular structure of certain compositions such as, for example, 25% (w/v) F127 of the present invention become more ordered.

In another embodiment of the present invention, a method of making a molecular separation device 2 has a hydrophobic surface. This method includes forming a channel 28 having first and second ends in the hydrophobic surface of the device 2, as described above. The surface of the channel 28 is treated sequentially with an oxidizing agent and a protophilic agent, as previously set forth. An acid-treated cover 34 is then fixed over the channel 28 to form a conduit 10.

A means for providing an electrophoretic charge is disposed between the first and second ends, respectively. This means for providing an electrophoretic charge may include, for example, a series of spaced apart electrodes 12, lead electrodes 24 and bond pads 26 for separating charged molecules, as described previously. Furthermore, this method includes introducing the present molecular separation medium into the conduit to prevent the electro-osmotic flow of a sample at the media-conduit interphase.

A further embodiment of the present invention sets forth a system for molecular separation within a conduit formed on a surface of a hydrophobic substrate, such as for example, a silicon wafer. This system includes a channel and a cover extending thereover to form a conduit as described previously. This channel is shaped and dimensioned for receiving the molecular separation medium of the present invention. The conduit is rendered competent to receive the molecular separation medium by modifying the surface thereof from hydrophobic to hydrophilic using the oxidation and protophilic reactions set forth above. This system further includes the present molecular separation medium disposed within the conduit, as well as, a means for providing an electrophoretic charge therethrough. In the present embodiment, the means for providing electrophoretic charge can include, for example, the electrodes 12, lead conductors 24 and pond pads 26, as previously set forth.

In yet a further embodiment of the present invention, a method is provided for rendering a material having a hydrophobic surface competent to separate molecular species. Any material can be used which has a hydrophobic surface that can be rendered hydrophilic by the oxidation and protophilic reactions of the present invention. For example, the material can be shaped and dimensioned into a device for conducting, e.g., molecular separations. This method includes treating the hydrophobic surface of such a device with an oxidizing agent followed by a protophilic agent to render the oxidized surface hydrophilic as described previously. This method also includes introducing the present molecular separation medium onto the hydrophilic surface of the device and changing the temperature thereof from the first operating temperature to the second operating temperature which renders the separation medium gel-like and able to adhere to the hydrophilic surface of the device. As set forth above, this ability of the separation medium to adhere to the surface-modified device prevents electro-osmotic flow of a charged sample around the medium instead of through it. Thus, accurate, efficient and high resolution separations can be obtained using this method.

In another embodiment of the present invention, a channel for electrophoretic molecular separation has a hydrophobic surface which is rendered hydrophilic through successive oxidation and protophilic reactions. This channel can be formed on a surface of a silicon wafer or a layer of silicon may be deposited on a surface of the channel to render it hydrophobic. Thus, this channel may be formed from any material compatible with the intended function of the present invention, provided that the channel surface is capable of supporting a hydrophobic surface, such as for example, a silicon surface.

Accordingly, the channel may be formed of a polymer, such as a plastic, followed by the deposition of a hydrophobic material, such as silicon, which is capable of being rendered hydrophilic by the processes set forth above. The hydrophobic material may be deposited on the surface of the channel by methods known in the art, such as for example, by dipping, spraying and vapor deposition.

In summary, the device, system and methods of the present invention are directed to separating charged molecules in an electric field. Through the oxidation and protophilic reactions described herein, a broad range of hydrophobic substrates can now be used in conjunction with the viscosity-adjustable molecular separation medium disclosed in the present invention to separate charged molecules in a medium under the influence of an electric field.

The following examples are set forth to illustrate the methods of the present invention used to render hydrophobic substrates hydrophilic. These examples are provided for purposes of illustration only and are not intended to be limiting in any sense.

EXAMPLE 1

Effects of Surface Treatment on Silicon

Preparation of Silicon Wafer
Modified Shiraki Treatment:
A 100 mm diameter silicon wafer (roughness=0.05 nm. thickness=0.015") having trapezoid-shaped channels etched into a surface thereof is treated as follows: (a) the silicon wafer is dipped into an oxidizing bath containing a 3:1 solution of $H_2O:HF$ at room temperature for 30 seconds; (b) the silicon wafer is removed from the oxidizing bath and rinsed in deionized water; (c) the silicon wafer is then dipped into a bath containing a 5:1:1 solution of $H_2O:H_2O_2:HCl$ at 80° C. for 5 minutes; (d) the silicon wafer is then removed from the bath and rinsed in deionized water; (e) steps (a)–(d) are repeated once; and (f) the silicon wafer is allowed to dry in $N_2$.
HCl Treatment:
Shiraki-treated and non-Shiraki treated silicon wafers are dipped into a protophilic bath containing 1N HCl for several seconds.
Polymer Treatment:
Untreated silicon wafers, Shiraki-treated only silicon wafers and Shiraki- and HCl-treated silicon wafers are dipped into a polymer solution containing 1% EPE in water for several seconds. The silicon wafer is dipped into $H_2O$ for several seconds and then allowed to dry in a stream of $N_2$.

EXAMPLE 2

Comparison of Molecular Separation Media Adsorbance to Hydrophobic v. Hydrophilic Silicon Surfaces On the surface of untreated silicon wafers, block copolymers did not uniformly attach thereto. Furthermore, no micellar structures were observed to form on the surface thereof. On silicon wafers treated with the Shiraki method alone as described in Example 1, some micellar structures were observed to form on the surface thereof. Such structures, however, were intermittent at best. On silicon wafers treated by the Shiraki method followed by the protophilic method of Example 1, however, a solid polymer layer was observed to form on the surface thereof which included an abundance of micellar structures.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:
1. A device for electrophoretic molecular separation comprising:
   a) a substrate with a surface having hydrophobic properties;
   b) a channel formed on said surface, said channel having an interior surface, said interior surface of said channel rendered hydrophilic through successive oxidation and protophilic reactions; and
   c) a cover extending over said channel to form a conduit;
   d) a molecular separation medium disposed in said conduit and positioned for application of an electric potential along the length of said interior of said conduit;
   wherein said separation medium comprises at least one block copolymer comprising a poly(oxybutylene) block segment.

2. The device of claim 1, wherein said at least one block copolymer is in solution at a first operating temperature and is in a gel-like state at a second operating temperature, and wherein said separation medium further comprises an operating buffer which dissolves said at least one block copolymer at said first operating temperature and which remains in said medium in said gel-like state without disruption of said molecular separation at said second operating temperature, said buffer rendering said at least one block copolymer dissolute upon return to said first operating temperature.

3. The device of claim 2, wherein said molecular separation medium in its gel-like state is adherent to said hydrophilic interior surface of said conduit.

4. The device of claim 2, wherein said at least one block copolymer is selected from the group consisting of di-block copolymers, tri-block copolymers, multi-block copolymers and mixtures thereof.

5. The device of claim 2, wherein said at least one block copolymer is described by
   Formula (I): $A_xB_y$;
   Formula (II): $A_xB_yA_z$;
   Formula (III): $B_xA_yB_z$;

Formula (IV): $A_xB_yC_z$; and mixtures thereof
wherein A, B and C are block segments and wherein A, B or C is poly(oxybutylene) and the remaining block segments are independently selected from the group consisting of poly(oxyethylene), poly(oxypropylene), polyacrylamide and poly(isopropyl) acrylamide; and x, y, and z are independently selected from whole numbers from about 1–10,000.

6. The device of claim 2, wherein said at least one block copolymer is further selected from the group consisting of $E_{41}B_8$, $B_{12}E_{260}B_{12}$, $E_{41}B_8$, $E_{45}B_{14}E_{45}$, $E_{79}B_{36}E_{79}$, and mixtures thereof wherein E is poly(oxyethylene) and B is poly(oxybutylene).

7. The device of claim 2, wherein said operating buffer is a good solvent for a first block segment of said block copolymer and is a marginal solvent, a poor solvent or a nonsolvent for a second block of said block copolymer.

8. The device of claim 7, wherein nonsolvated block segments of said block copolymer self-assemble into said gel-like state.

9. The device of claim 2, wherein said operating buffer is selected from the group consisting of 1× TBE and tris-glycine buffers.

10. The device of claim 2, wherein said first operating temperature is a temperature which is not destructive of said block copolymer and which is characterized by a low viscosity of said block copolymer.

11. The device of claim 2, wherein said second operating temperature is a temperature which is not destructive of said block copolymer.

12. The device of claim 2, wherein said block copolymer further comprises a poly(oxypropylene) block segment.

13. The device of claim 12, wherein said first operating temperature is from about 15° C. to about 1° C.

14. The device of claim 12, wherein said second operating temperature is above about 20° C.

15. The device of claim 1, wherein said substrate is a silicon wafer.

16. The device of claim 1, wherein an oxidizing agent selected from the group consisting of hydrogen fluoride, ozone, permanganate ion, nitric acid, oxygen and mixtures thereof provides said conduit with an oxidized surface.

17. The device of claim 1, wherein an acid produces said protophilic reaction to render said oxidized surface hydrophilic.

18. The device of claim 1, wherein said oxidation and protophilic reactions are produced with HF and HCl, respectively.

19. A device for electrophoretic molecular separation comprising:
   a) a substrate with a surface having hydrophobic properties;
   b) a channel formed on said surface, said channel having an interior surface, said interior surface of said channel rendered hydrophilic through successive oxidation and protophilic reactions; and
   c) a cover extending over said channel to form a conduit;
   d) a molecular separation medium disposed in said conduit and positioned for application of an electric potential along the length of said interior of said conduit;
   wherein said separation medium comprises at least two block copolymers which are in solution at a first operating temperature and are in a gel-like state at a second operating temperature, and an operating buffer which dissolves said at least two block copolymers at said first operating temperature and which remains in said medium in said gel-like state without disruption of said molecular separation, said buffer rendering said at least two block copolymers dissolute upon return to said first operating temperature.

20. A device for electrophoretic molecular separation comprising:
   a) a substrate with a surface having hydrophobic properties;
   b) a channel formed on said surface, said channel having an interior surface, said interior surface of said channel rendered hydrophilic through successive oxidation and protophilic reactions;
   c) a cover extending over said channel to form a conduit;
   d) a molecular separation medium disposed within said conduit and positioned for application of an electric potential along the length of said interior of said conduit, wherein said molecular separation medium comprises about 25% (w/v) $E_{99}P_{69}E_{99}$ in 1× TBE buffer.

21. A method of making a device for molecular separation, said device having a hydrophobic surface comprising:
   a) forming a channel in said hydrophobic surface, said channel having a first and a second end;
   b) treating a surface of said channel with an oxidizing agent to form an oxidized surface within said channel;
   c) treating said oxidized surface with a protophilic agent to form a hydrophilic surface within said channel;
   d) fixing a cover over said channel which has been processed according to steps a, b and c above to form a conduit;
   e) disposing a molecular separation medium within said conduit;
   wherein said separation medium comprises at least one block copolymer comprising a poly(oxybutylene) block segment.

22. The method of claim 21, further comprising disposing a means for providing an electrophoretic charge between said first and second ends.

23. The method of claim 21, wherein said at least one block copolymer is in solution at a first operating temperature and is in a gel-like state at a second operating temperature, and wherein said molecular separation medium further comprises an operating buffer which dissolves said at least one block copolymer at said first operating temperature and which remains in said medium in said gel-like state without disruption of said molecular separation at said second operating temperature, said buffer rendering said at least one block copolymer dissolute upon return to said first operating temperature.

24. The method of claim 23, wherein said block copolymer is selected from the group consisting of di-block copolymers, tri-block copolymers, multi-block copolymers and mixtures thereof.

25. The method of claim 23, wherein said block copolymer is described by
   Formula (I): $A_xB_y$;
   Formula (II): $A_xB_yA_z$;
   Formula (III): $B_xA_yB_z$;
   Formula (IV): $A_xB_yC_z$; and mixtures thereof
wherein A, B and C are block segments wherein A, B or C is poly(oxybutylene) and the remaining block segments are independently selected from the group consisting of poly (oxyethylene), poly(oxypropylene), polyacrylamide and poly(isopropyl) acrylamide,; and x, y, and z are independently selected from whole numbers from about 1–10,000.

26. A system for molecular separation within a conduit formed on a surface of a hydrophobic substrate comprising:
  a) a channel having a modified hydrophobic surface shaped and dimensioned for receiving a molecular separation medium and a cover extending over said channel to form said conduit, wherein said modified hydrophobic surface is hydrophilic and is competent for molecular separation;
  b) a molecular separation medium disposed within said conduit wherein said separation medium comprises at least one block copolymer comprising a poly(oxybutylene) block segment; and
  c) a means for providing an electrophoretic charge therethrough.

27. The system of claim 26, wherein said substrate is a silicon wafer.

28. The system of claim 27, wherein said modified hydrophobic surface is modified by an oxidation reaction and an acid treatment to provide a hydrophilic surface.

29. The system of claim 26, wherein said at least one block copolymer is in solution at a first operating temperature and is in a gel-like state which is able to adhere to said hydrophilic silica channel surface at a second operating temperature, wherein said molecular separation medium further comprises an operating buffer which dissolves said at least one block copolymer at said first operating temperature and which remains in said medium in said gel-like state without disruption of said molecular separation at said second operating temperature, said buffer rendering said at least one block copolymer dissolute upon return to said first operating temperature.

30. The system of claim 26, wherein said means for providing electrophoretic charge includes an anode at a first end of said conduit and a cathode at a second end of said conduit, said second end being spaced apart from said first end.

31. A method of rendering a device having a hydrophobic surface competent to separate molecular species in a molecular separation medium comprising:
  a) treating said hydrophobic surface with an oxidizing agent;
  b) treating said oxidizing surface with a protophilic agent to render said surface hydrophilic;
  c) introducing said separation medium onto said hydrophilic surface, said separation medium comprising at least one block copolymer which is in solution at a first operating temperature and is in a gel-like state at a second operating temperature, and an operating buffer which dissolves said at least one block copolymer at said first operating temperature and which remains in said medium in said gel-like state without hindering the separation of said molecular species at said second operating temperature, said buffer rendering said at least oe block copolymer dissolute upon return to said first operating temperature; and
  d) changing the temperature of said separation medium from said first operating temperature to said second operating temperature which renders said separation medium gel-like and able to adhere to said hydrophilic surface;
  wherein said separation medium comprises at least one block copolymer comprising a poly(oxybutylene) block segment.

* * * * *

UNITED STATES PATENT AND TRADEMARK OFFICE
CERTIFICATE OF CORRECTION

PATENT NO. : 5,989,399
DATED : November 23, 1999
INVENTOR(S) : Benjamin Chu, et al.

It is certified that error appears in the above-identified patent and that said Letters Patent is hereby corrected as shown below:

Column 18, line 22, now reads: "least oe block copolymer dissolute upon return to said"
should read: "least one block copolymer dissolute upon return to said"-

Signed and Sealed this

Eighteenth Day of July, 2000

Attest:

Q. TODD DICKINSON

*Attesting Officer*          *Director of Patents and Trademarks*